United States Patent
Jia et al.

(10) Patent No.: US 12,233,036 B2
(45) Date of Patent: Feb. 25, 2025

(54) INHIBITORS OF AUTOPHAGY AND DCAR-1 AS NOVEL ANTHELMINTIC AGENTS

(71) Applicant: FLORIDA ATLANTIC UNIVERSITY BOARD OF TRUSTEES, Boca Raton, FL (US)

(72) Inventors: Kailiang Jia, Boca Raton, FL (US); Thomas Parker, Boca Raton, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 251 days.

(21) Appl. No.: 16/724,467

(22) Filed: Dec. 23, 2019

(65) Prior Publication Data

US 2020/0268697 A1    Aug. 27, 2020

Related U.S. Application Data

(60) Provisional application No. 62/808,602, filed on Feb. 21, 2019.

(51) Int. Cl.
  *A61K 31/192* (2006.01)
  *A61P 33/10* (2006.01)
  *A61K 45/06* (2006.01)

(52) U.S. Cl.
  CPC ............ *A61K 31/192* (2013.01); *A61P 33/10* (2018.01); *A61K 45/06* (2013.01)

(58) Field of Classification Search
  None
  See application file for complete search history.

(56) References Cited

U.S. PATENT DOCUMENTS

| | | | | |
|---|---|---|---|---|
| 3,663,693 A | * | 5/1972 | Slighter et al. | A61K 31/00 514/157 |
| 2004/0229908 A1 | * | 11/2004 | Nelson | A61K 31/4706 514/313 |
| 2017/0258929 A1 | * | 9/2017 | Cardelli | A61P 43/00 |

OTHER PUBLICATIONS

Chemical Abstract Registry No. 54-05-7, indexed in the Registry File on STN CAS Online Nov. 16, 1984.*
Berge et al., Pharmaceutical Salts. Journal of Pharmaceutical Sciences, 1977, 66, 1-19.*
Veldhoen et al., The chemotherapeutic agent paclitaxel inhibits autophagy through two distinct mechanisms that regulate apoptosis. Oncogene, 2013, 32, 736-746.*
Blaxter et al. (1997). Chapter 30: Parasitic Nematodes in C. elegans II, eds Riddle DL et al. Cold Spring Harbor aboratory Press (NY), 2nd Ed. 1-29.
Buerglin et al. (1998) Caenorhabditis elegans as a model for parasitic nematodes. International Journal for Parasitology 28, 395-411.
Golden et al. (1984). A pheromone-induced developmental switch in Caenorhabditis elegans: Temperature-sensitive mutants reveal a wild-type temperature-dependent process. Proc. Natl. Acad. Sci. USA, 81, 819-823.
Holden-Dye et al. (2007) Anthelmintic drugs. WormBook, 1-13.
Jasmer et al. (2003) Parasitic nematode interactions with mammals and plants. Annu. Rev. Phytopathol. 41, 245-270.
Melendez et al. (2003). Autophagy genes are essential for dauer development and life-span extension in C. elegans. Science, 301, 1387-1391.
Tissenbaum et al. (2000). A common muscarinic pathway for diapause recovery in the distantly related nematode species *Caenorhabditis elegans* and *Ancylostoma caninum*. PNAS, 97(1), 460-465.

* cited by examiner

*Primary Examiner* — Po-Chih Chen

(74) *Attorney, Agent, or Firm* — Meunier Carlin & Curfman LLC

(57) ABSTRACT

Methods and compositions for controlling parasitic nematodes and treating or preventing a parasitic nematode infection are described herein. The methods include the use of compositions containing an autophagy inhibitor and/or a DCAR-1 inhibitor as anthelmintic agents.

8 Claims, 3 Drawing Sheets

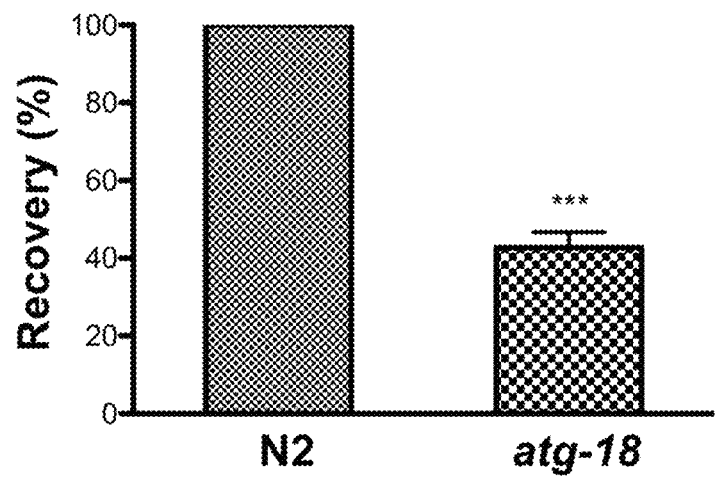
Fig. 3
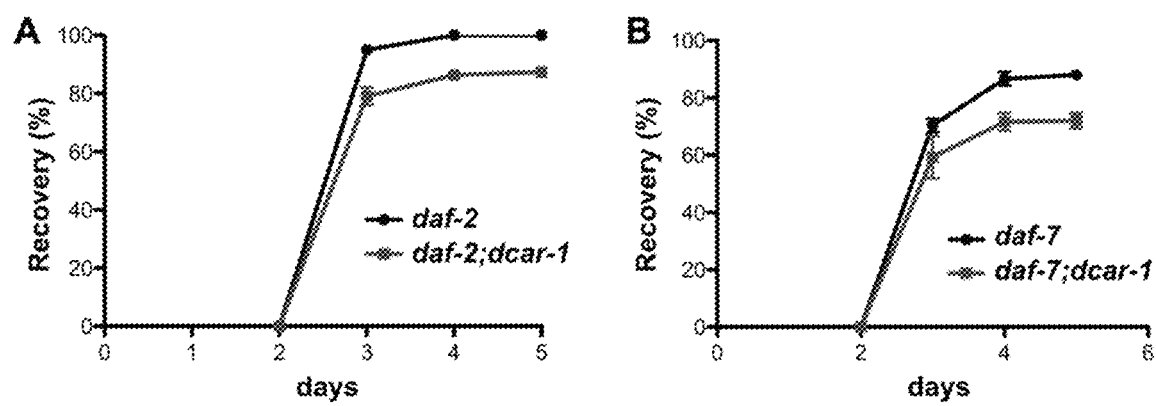
Fig. 4A
Fig. 4B

INHIBITORS OF AUTOPHAGY AND DCAR-1 AS NOVEL ANTHELMINTIC AGENTS

CROSS-REFERENCE TO RELATED APPLICATIONS

This application claims the benefit of U.S. Application Ser. No. 62/808,602, filed Feb. 21, 2019, the contents of which are incorporated herein by reference in their entireties for all purposes.

STATEMENT REGARDING FEDERALLY SPONSORED RESEARCH OR DEVELOPMENT

This invention was made with government support under Grant No. 1R15HD080497-01 awarded by the National Institutes of Health (NIH). The government has certain rights in the invention.

FIELD OF INVENTION

This invention relates to the use of autophagy and DCAR-1 inhibitors as anthelmintic agents.

BACKGROUND OF THE INVENTION

Parasitic nematodes can infect humans, animals, and plants. Approximately one billion people worldwide are infected by nematode parasites. Each year, the loss of billions of dollars is attributed to parasitic nematodes in agriculture and the livestock industry. (Jasmer D P, Goverse A, & Smant G (2003) Parasitic nematode interactions with mammals and plants. *Annu Rev Phytopathol* 41:245-270.)

Anthelmintic drugs are used to treat infections with parasitic worms including flat worms and round worms. They are important for human tropical medicine, veterinary medicine and agriculture. Table 1 below lists common drugs used in human and veterinary medicine to treat parasitic nematode infection. Most of the anthelmintic drugs cause paralysis of nematode parasites to prevent them from entering the body of the host. (Holden-Dye L & Walker R J (2007) Anthelmintic drugs. *WormBook:* 1-13.)

TABLE 1

Mechanisms of action for common anthelmintic drugs

| Drugs | Mechanisms of action |
|---|---|
| Piperazine | weak GABA-mimetic and causes paralysis of body |
| Benzamidazoles | compromise the cytoskeleton through a selective interaction with β-tubulin and causes paralysis of body |
| Levamisole, Pyrantel and Morantel | nicotinic receptor agonists and causes paralysis of body |
| Paraherquamide | antagonists on acetylcholine-stimulated body wall muscle contractions and causes paralysis of body |
| Ivermectin | activates glutamate-gated chloride channels (GluCl) and causes paralysis of body |
| Emodepside | stimulates excessive neurotransmitter release at neuromuscular site and causes paralysis of body |
| Nitazoxanide | a pyruvate ferredoxin oxidoreductase inhibitor and the site of action of this compound has not been established in nematodes |

Although anthelmintic drugs have been developed to treat nematode infections, drug resistance has been a growing concern. (Jasmer, supra.) Anthelmintic resistant strains of parasites are an increasing threat to livestock and humans and there exists a need for new safe and effective anthelmintic agents.

SUMMARY OF THE INVENTION

A first aspect of the invention comprises an anthelmintic composition comprising at least one of an autophagy inhibitor and a DCAR-1 inhibitor, wherein the anthelmintic composition is effective to suppress at least one of growth and propagation of a nematode.

In certain embodiments, the autophagy inhibitor is effective to inhibit or induce a kinase that affects autophagy.

In certain embodiments, the autophagy inhibitor is effective to suppress autolysosome formation.

In certain embodiments, the autophagy inhibitor is at least one member selected from the group consisting of Autophinib, Azithromycin, ARN5187, AS 1842856, autophagy inhibitor VII, Bafilomycin A1, (±)-Bay K 8644, 3BDO, Chloroquine, Concanamycin A, CA-5f, Daurisoline, DBeQ, E 64d, DC661, EAD1, Edaravone, EZSOLUTION™ Gö 6976; (5,6,7,13-Tetrahydro-13-methyl-5-oxo-12H-indolo[2,3-a]pyrrolo[3,4-c]carbazole-12-propanenitrile, aka Gö 6976), GMX1778, GW 4064, Hydroxychloroquine Sulfate, IITZ-01, KU-55933, L-Asparagine, Leupeptin BioUltra, Liensinine, Lucanthone, LY 294002 hydrochloride, Lys01 trihydrochloride, Lys05, Mdivi 1, 3-methyladenine, MHY1485, ML 240, MRT 67307 dihydrochloride, MRT 68601 hydrochloride, MRT 68921 dihydrochloride, NMS 873, Nocodazole, NSC18505 Paclitaxel, PD98059, Pepstatin A, PFK15, PFK158, PHY34, PIK-III, Rapamycin, ROC-325, SAR-405, SB202190, SB203580, SBI-0206965, SP600125, Sinomenine, Spautin 1, TAXOL (NSC125973 Paclitaxel), Thapsigargin, ULK-101, U0126, Vinblastine sulfate, Wortmannin and Xanthohumol.

In certain embodiments, the DCAR-1 inhibitor is a structural analog of dihydrocaffeic acid.

In certain embodiments, the anthelmintic composition comprises both the autophagy inhibitor and the DCAR-1 inhibitor.

In certain embodiments, the anthelmintic composition comprises the autophagy inhibitor in an amount of 1 to 1000 µg/ml and the DCAR-1 inhibitor in an amount of 1 to 1000 µg/ml.

In certain embodiments, the anthelmintic composition further comprises a pharmaceutically acceptable excipient.

In certain embodiments, the anthelmintic composition further comprises an agriculturally acceptable excipient.

A second aspect of the invention comprises a method for suppressing growth of a nematode, said method comprising exposing the nematode to the anthelmintic composition of the invention so as to suppress at least one of growth and propagation of the nematode.

In certain embodiments of the inventive method, the autophagy inhibitor inhibits or induces a kinase that affects autophagy.

In certain embodiments of the inventive method, the autophagy inhibitor suppresses autolysosome formation.

In certain embodiments of the inventive method, the autophagy inhibitor is at least one member selected from the group consisting of Autophinib, Azithromycin, ARN5187, AS 1842856, autophagy inhibitor VII, Bafilomycin A1, (±)-Bay K 8644, 3BDO, Chloroquine, Concanamycin A, CA-5f, Daurisoline, DBeQ, E 64d, DC661, EAD1, Edaravone, EZSOLUTION™ Gö 6976, (5,6,7,13-Tetrahydro-13-methyl-5-oxo-12H-indolo[2,3-a]pyrrolo[3,4-c]carbazole-12-propanenitrile, aka Gö 6976), GMX1778, GW 4064, Hydroxychloroquine Sulfate, IITZ-01, KU-55933, L-Asparagine, Leupeptin BioUltra, Liensinine, Lucanthone, LY 294002 hydrochloride, Lys01 trihydrochloride, Lys05, Mdivi 1, 3-methyladenine, MHY1485, ML 240, MRT 67307 dihydrochloride, MRT 68601 hydrochloride, MRT 68921 dihydrochloride, NMS 873, Nocodazole, NSC18505 Paclitaxel, PD98059, Pepstatin A, PFK15, PFK158, PHY34, PIK-III, Rapamycin, ROC-325, SAR-405, SB202190, SB203580, SBI-0206965, SP600125, Sinomenine, Spautin 1, TAXOL (NSC125973 Paclitaxel), Thapsigargin, ULK-101, U0126, Vinblastine sulfate, Wortmannin and Xanthohumol.

In certain embodiments of the inventive method, the DCAR-1 inhibitor is a structural analog of dihydrocaffeic acid.

In certain embodiments of the inventive method, the anthelmintic composition comprises both the autophagy inhibitor and the DCAR-1 inhibitor.

In certain embodiments of the inventive method, the anthelmintic composition comprises the autophagy inhibitor in an amount of 1 to 1000 µg/ml and the DCAR-1 inhibitor in an amount of 1 to 1000 µg/ml In certain embodiments of the inventive method, the anthelmintic composition is administered to a human or animal.

In certain embodiments of the inventive method, the anthelmintic composition is applied to a plant, a seed or soil.

BRIEF DESCRIPTION OF THE DRAWINGS

FIG. 3 is a bar graph showing that atg-18 mutations suppress recovery of wild type dauer larvae (*** P<0.0001, t-test).

FIG. 4A shows that dcar-1 mutations suppress recovery of daf-2 dauer larvae.

FIG. 4B shows that dcar-1 mutations suppress recovery of daf-7 (B) dauer larvae.

DETAILED DESCRIPTION OF PREFERRED EMBODIMENTS

The infectious larvae of parasitic nematodes invade the host and resume development to adult parasites, a process analogous to the recovery of C. elegans dauer larvae (Burglin T R, Lobos E, & Blaxter M L (1998) Caenorhabditis elegans as a model for parasitic nematodes. International journal for parasitology 28(3):395-411). Thus, a fundamental understanding of the mechanisms that underlie the dauer state in C. elegans will illuminate methods for the control of nematode parasites (Blaxter M & Bird D (1997) Parasitic Nematodes. C. elegans II, eds Riddle D L, Blumenthal T, Meyer B J, & Priess JRCold Spring Harbor (NY)), 2nd Ed.).

At least three environmental cues have been identified that control C. elegans dauer entry and recovery: food supply, temperature, and a constitutively secreted dauer-inducing pheromone that signals population density. A high ratio of pheromone to food favors both dauer larvae formation and maintenance of dauer state, whereas a low ratio favors continuous growth and stimulates dauer larvae to recover. Temperature modulates the response to the food/pheromone ratio, with higher growth temperature favoring the dauer state (Golden J W & Riddle D L (1984) A pheromone-induced developmental switch in Caenorhabditis elegans: Temperature-sensitive mutants reveal a wild-type temperature-dependent process. Proc Natl Acad Sci USA 81(3):819-823). Molecular studies of dauer mutants revealed that two neural pathways control the developmental response to dauer-inducing environmental cues. Specifically, these two pathways are the DAF-7/transforming growth factor-β (TGF-β) and DAF-2/insulin growth factor-like (IGF) pathways. Research with C. elegans suggests that host or parasite insulin-like signals may regulate recovery of parasitic nematode Ancylostoma caninum (Tissenbaum H A, et al. (2000) A common muscarinic pathway for diapause recovery in the distantly related nematode species Caenorhabditis elegans and Ancylostoma caninum. Proc Natl Acad Sci USA 97(1):460-465).

Figure 1:
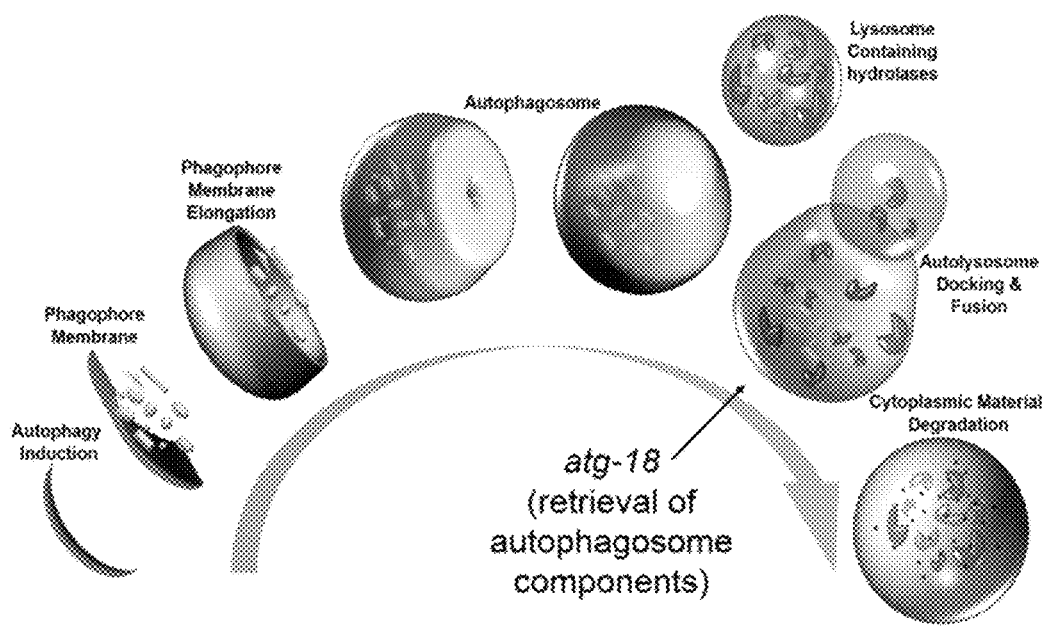
FIG. 1 is a schematic illustration of the autophagy process in yeast and mammalian cells. ATG-18 is the autophagy protein used for examination of autophagy function.

Autophagy (derived from the Greek meaning "to eat oneself") is an evolutionarily conserved lysosomal degradation pathway. It is present in all eukaryotic cells and conserved from yeast to humans. As seen in FIG. 1, the autophagy process involves the formation of a double-membrane structure called the autophagosome, which involves sequential steps including induction, vesicle nucleation, vesicle expansion and completion, and retrieval that are then followed by fusion with the lysosome and degradation of the sequestered contents. The resulting breakdown products, such as amino acids and free fatty acids, are released into the cytosol and recycled to synthesize new macromolecules and to maintain cellular energy homeostasis.

Figure 2:
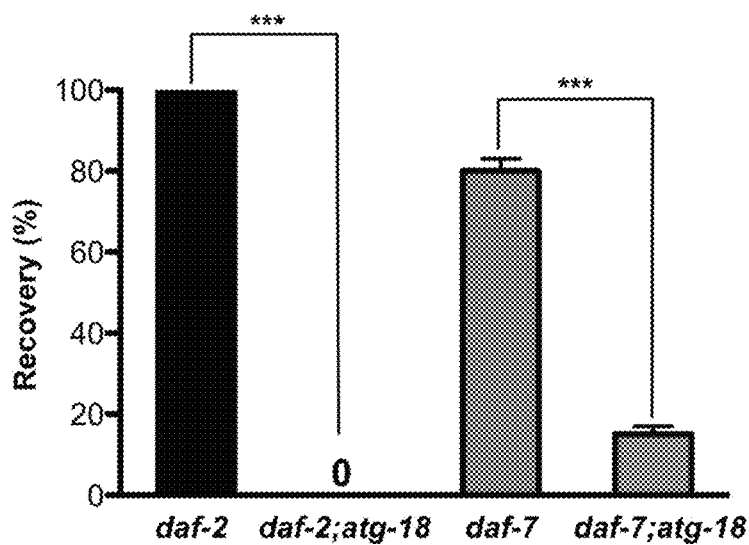
FIG. 2 is a bar graph showing that atg-18 mutations suppress recovery of daf-2 and daf-7 mutant dauer larvae (***P<0.0001, t-test, daf-2 vs. daf-2; atg-18 and daf-7 vs. daf-7; atg-18).

C. elegans is an exceptionally tractable and informative model system for parasitic nematodes (Holden-Dye, supra). In C. elegans, autophagy is enhanced during dauer formation (Melendez A, et al. (2003) Autophagy genes are essential for dauer development and life-span extension in C. elegans. Science 301(5638):1387-1391). Furthermore, inactivation of C. elegans autophagy genes (e.g., C. elegans orthologs of yeast ATG1, ATG6, ATG7, ATG8, and ATG18) does not affect dauer initiation, but partially blocks morphogenetic and physiological features of dauer development (Id.). We have surprisingly found that autophagy is required for recovery of C. elegans dauer larvae.

daf-2 encodes the worm ortholog of an insulin-like receptor. daf-2 mutants form dauer larvae constitutively at 25° C. daf-2 dauers recover and develop to fertile adults at 15° C., the permissive temperature for daf-2 mutants. As seen in FIG. 2, we found mutations in the atg-18 gene completely block recovery of daf-2 dauer larvae. DAF-7 is a member of the TGF-β protein family and daf-7 mutants form dauer constitutively at 25° C. We found that 75% of daf-7 mutant dauer larvae recover at 15° C. Interestingly, atg-18 mutations significantly decrease the recovery of daf-7 mutant dauer larvae by more than 50%.

Finally, we found atg-18 mutations inhibit recovery of wild type dauer larvae. We transferred atg-18 dauer larvae formed by pheromone treatment to fresh worm food plates and scored dauer recovery. Experiment was done at 20° C., the standard temperature for growing up worms. As seen in FIG. 3, we found 100% of N2 dauers recovered. By contrast, only 46% of atg-18 dauer larvae recovered. The data indicates that inhibition of autophagy blocks recovery of dauer larvae. Thus, by inhibiting autophagy, while nematode parasites can infect a host, the parasites could not grow up to adults to produce progeny.

Figure 5:
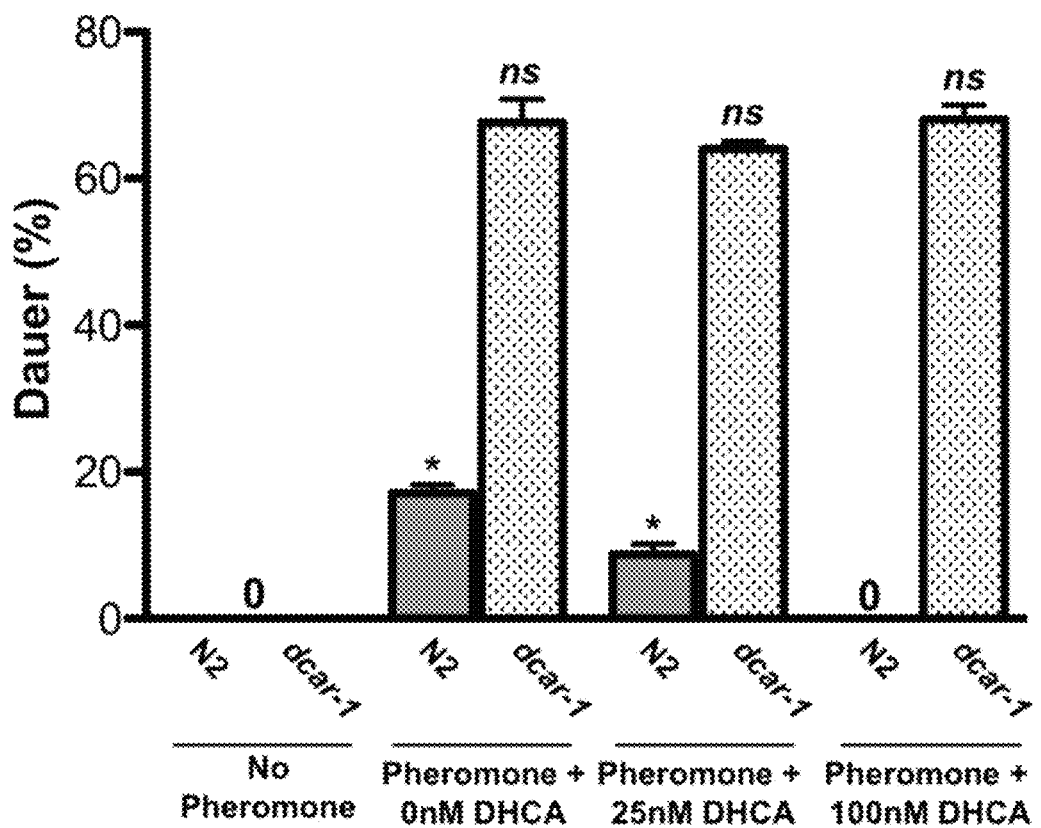
FIG. 5 is a bar graph showing that dihydrocaffeic acid (DHCA) is the ligand for DCAR-1 GPCR. DHCA is the food signal that competes with the dauer-inducing pheromone to suppress dauer formation. (*P<0.01, t-test, N2 treated with 0 nM DHCA compared to N2 treated with 25 nM DHCA and N2 treated with 25 nM DHCA compared to N2 treated with 100 nM DHCA. ns, no statistical significant difference.)

Recovery of dauer larvae requires the presence of food. G protein-coupled receptors (GPCRs) detect molecules such as food odors and activate internal signal transduction pathways. We identified a GPCR, DCAR-1, which is involved in detection of food signals in C. elegans. As seen in FIG. 4, we found that mutations of dcar-1 significantly suppress the recovery of daf-2 and daf-7 mutant dauer larvae. The recovery percentage of daf-2 and daf-7 mutant dauer larvae decreased by 25% when dcar-1 is mutated. Dihydrocaffeic acid (DHCA) is the ligand for DCAR-1. As seen in FIG. 5, DHCA can mimic food signals and counteract the effect of pheromone on dauer formation. When wild type C. elegans was treated by pheromone, around 20% of animals entered dauer. However, in the presence of 25 nM DHCA, the percentage of dauer was decreased to 5%. When treated with 100 nM DHCA, none of animals formed dauer in the presence of pheromone. Thus, DCAR-1 inhibitors act to block detection of foods signals by infective nematode parasites and to suppress the growth of parasites to adults.

We surprisingly found that by targeting autophagy and DCAR-1, inhibitors of autophagy and DCAR-1 suppress recovery of infective nematode parasites and stop the propagation of parasites inside the host. Inhibition of autophagy and DCAR-1 is a completely new mechanism of action different from available anthelmintic drugs that cause body paralysis of nematode parasites.

Autophagy and DCAR-1 inhibitors may be used to control parasitic nematodes in a plant. By "control," we mean to prevent, treat, reduce, suppress or control growth and propagation of parasitic nematodes in plants. This may be done by mixing the inhibitor with seeds, fertilizer and soil at any stage of planting or by any other means whereby the inhibitor is delivered inside a plant.

Similarly, autophagy and DCAR-1 inhibitors may be used to treat or prevent parasitic nematode infections in a subject, human or animal. In particular, an autophagy inhibitor may be used to prevent parasitic nematode infection by suppressing the development of the infective stage of nematode parasites. Autophagy and DCAR-1 inhibitors may also be used to suppress growth and propagation of nematode parasites inside an infected host.

Autophagy inhibitors for use as anthelmintic agents may include agents that inhibit or induce kinases that affect autophagy (such as phosphoinositide 3-kinase (PI3) and mammalian target of rapamycin (mTOR)) or agents that target the late state of the autophagy process-autolysosome formation. These include, but are not limited to, agents, such as, for example, Autophinib, Azithromycin, ARN5187, AS 1842856, autophagy inhibitor VII, Bafilomycin A1, (±)-Bay K 8644, 3BDO, Chloroquine, Concanamycin A, CA-5f, Daurisoline, DBeQ, E 64d, DC661, EAD1, Edaravone, EZSOLUTION™ Gö 6976-(5.6.7,13-Tetrahydro-13-methyl-S-oxo-12H-indolo[2,3-a]pyrrolo[3,4-c]carbazole-12-propanenitrile, aka Gö 6976), GMX1778, GW 4064, Hydroxychloroquine Sulfate, IITZ-01, KU-55933, L-Asparagine, Leupeptin BioUltra, Liensinine, Lucanthone, LY 294002 hydrochloride, Lys01 trihydrochloride, Lys05, Mdivi 1, 3-methyladenine, MHY1485, ML 240, MRT 67307 dihydrochloride, MRT 68601 hydrochloride, MRT 68921 dihydrochloride, NMS 873, Nocodazole, NSC18505 Paclitaxel, PD98059, Pepstatin A, PFK15, PFK158, PHY34, PIK-III, Rapamycin, ROC-325, SAR-405, SB202190, SB203580, SBI-0206965, SP600125, Sinomenine, Spautin 1, TAXOL (NSC125973 Paclitaxel), Thapsigargin, ULK-101, U0126, Vinblastine sulfate, Wortmannin and Xanthohumol.

The autophagy inhibitor is preferably present at a concentration of 1 ng/ml to 1 g/ml. In certain embodiments, the concentration of autophagy inhibitor ranges from a minimum of 1 ng/ml, 10 ng/ml, 100 ng/ml, 1 µg/ml, 10 µg/ml, 100 µg/ml, 1 mg/ml, 10 mg/ml or 100 mg/ml to a maximum of 10 ng/ml, 100 ng/ml, 1 µg/ml, 10 µg/ml, 100 µg/ml, 1 mg/ml, 10 mg/ml, 100 mg/ml or 1 g/ml.

Figure 6:
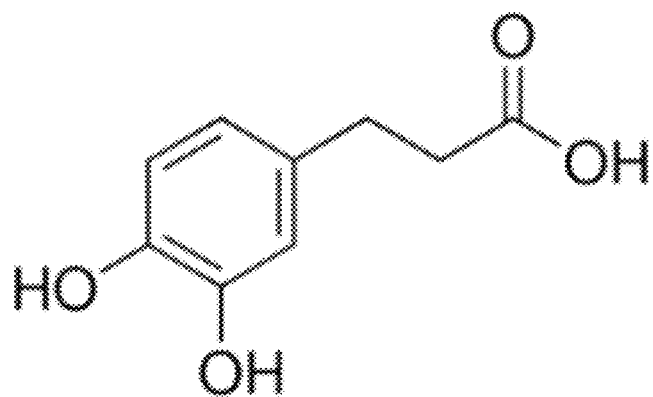
FIG. 6 shows the structure of DHCA.

DCAR-1 inhibitors may be used as anthelmintic agents with or without autophagy inhibitors. Preferred DCAR-1 inhibitors are structural analogs of DHCA (see FIG. 6).

In certain embodiments, the structural analogs have one or more hydrogen atoms of DHCA replaced by one substituent or several (e.g., 2, 3, 4, 5, 6, 7, 8, 9 or 10) substituents as defined below. Suitable substituents include but are not limited to halogen, —CN, —NO$_2$, oxo (=O), —OR, —SR, —N(R)$_2$, —NRC(O)R, —SO$_2$R, —SO$_2$OR, —SO$_2$N(R)$_2$, —C(O)R, —C(O)OR, —C(O)N(R)$_2$, C$_{1-6}$ alkyl, C$_{1-6}$ haloalkyl, C$_{1-6}$ alkoxy, C$_{2-8}$ alkenyl, C$_{2-8}$ alkynyl, C$_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted, and wherein R at each occurrence is independently hydrogen, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl.

The DCAR-1 inhibitor is preferably present at a concentration of 1 ng/ml to 1 g/ml. In certain embodiments, the concentration of DCAR-1 inhibitor ranges from a minimum of 1 ng/ml, 10 ng/ml, 100 ng/ml, 1 µg/ml, 10 µg/ml, 100 µg/ml, 1 mg/ml, 10 mg/ml or 100 mg/ml to a maximum of 10 ng/ml, 100 ng/ml, 1 µg/ml, 10 µg/ml, 100 µg/ml, 1 mg/ml, 10 mg/ml, 100 mg/ml or 1 g/ml.

In general, anthelmintic compositions of the invention comprise one or more ingredients additional to the autophagy inhibitor and/or DCAR-1 inhibitor. In particular, the compositions preferably include an excipient suitable for the intended use of the composition.

As used herein, the term "excipient" refers to ingredients which are used in the practice of formulating a safe and effective composition. Excipients are used primarily to serve in delivering a safe, stable, and functional composition, serving not only as part of the overall vehicle for delivery but also as a means for achieving effective delivery of the active agent(s) to the target organisms.

Examples of pharmaceutically acceptable excipients are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Suitable excipients include but are not limited to binding agents, buffers, colors, compression aids, diluents, disintegrants, emulsifiers, encapsulating materials, fillers, flavoring agents, flours, gelatins, glidants, gums, inert fillers, lubricants, preservatives, solubilizers, stabilizers, starches, sugars, surface modifying agents (including surfactants), suspending agents, stabilizing agents, sweeteners, tablet-disintegrating agents, thickening agents and viscosity regulators.

While the invention has been described in detail and with reference to specific examples thereof, it will be apparent to one skilled in the art that various changes and modifications can be made therein without departing from the spirit and scope thereof.

What is claimed is:

1. An anthelmintic composition comprising an active agent and an excipient,
   wherein the active agent consists of an autophagy inhibitor and a DCAR-1 inhibitor,
   wherein the DCAR-1 inhibitor is dihydrocaffeic acid.

2. The anthelmintic composition of claim 1, wherein the autophagy inhibitor is present in an amount of 1 to 1000 µg/ml and the DCAR-1 inhibitor is present in an amount of 1 to 1000 µg/ml.

3. The anthelmintic composition of claim 1, wherein the excipient is a pharmaceutically acceptable excipient.

4. The anthelmintic composition of claim 1, wherein the excipient is an agriculturally acceptable excipient.

5. An anthelmintic composition comprising an active agent and an excipient, wherein the active agent consists of dihydrocaffeic acid and an anthelmintic agent selected from the group consisting of autophinib, azithromycin, ARN5187, AS1842856, autophagy inhibitor VII, bafilomycin Al, (±)-Bay K8644, 3BDO, chloroquine, concanamycin A, CA-5f, daurisoline, DBeQ, E64d, DC661, EAD1, edaravone, 5,6,7,13-tetrahydro-13-methyl-5-oxo-12H-indolo[2,3-a]pyrrolo[3,4-c]carbazole-12-propanenitrile, GMX1778, GW4064, hydroxychloroquine sulfate, IITZ-01, KU-55933, L-asparagine, leupeptin, liensinine, lucanthone, LY294002 hydrochloride, Lys0I trihydrochloride, Lys05, Mdivi-1, 3-methyladenine, MHY1485, ML240, MRT67307 dihydrochloride, MRT68601 hydrochloride, MRT68921 dihydrochloride, NMS873, nocodazole, paclitaxel, PD98059, pepstatin A, PFK15, PFK158, PHY34, PIK-III, rapamycin, ROC-325, SAR-405, SB202190, SB203580, SBI-0206965, SP600125, sinomenine, spautin 1, thapsigargin, ULK-101, U0126, vinblastine sulfate, wortmannin, and xanthohumol.

6. The anthelmintic composition of claim 5, wherein the dihydrocaffeic acid is present in an amount of 1 to 1000 µg/ml.

7. The anthelmintic composition of claim 5, wherein the excipient is a pharmaceutically acceptable excipient.

8. The anthelmintic composition of claim 5, wherein the excipient is an agriculturally acceptable excipient.

* * * * *